US006040475A

United States Patent [19]
Pfander et al.

[11] Patent Number: 6,040,475
[45] Date of Patent: Mar. 21, 2000

[54] INTERMEDIATE COMPOUNDS FOR MAKING METABOLITES OF LYCOPENE

[75] Inventors: Hanspeter Pfander, Bern; Bruno Traber, Münsingen, both of Switzerland

[73] Assignee: Roche Vitamins Inc., Nutley, N.J.

[21] Appl. No.: 09/310,280

[22] Filed: May 12, 1999

Related U.S. Application Data

[62] Division of application No. 09/168,143, Oct. 7, 1998.

[30] Foreign Application Priority Data

Oct. 20, 1997 [EP] European Pat. Off. .............. 97118144
Aug. 13, 1998 [EP] European Pat. Off. .............. 98115249

[51] Int. Cl.$^7$ ........................ C07C 67/02; C07C 49/105; C07C 35/06
[52] U.S. Cl. .......................... 560/264; 560/129; 560/231; 568/379; 568/838
[58] Field of Search .................................... 560/129, 264, 560/231; 568/379, 838

[56] References Cited

U.S. PATENT DOCUMENTS 3,781,314 12/1973 Bollag .
5,166,445 11/1992 Meyer .

FOREIGN PATENT DOCUMENTS 382 067 8/1990 European Pat. Off. .
25 54 924 6/1977 Germany .

OTHER PUBLICATIONS

Houben–Weyl, "Ketone II ", Methoden der org. Chem., vol. 7, Part 2B, pp. 1448–1487, 1980.
J. Bertram, "The chemoprevention of cancer by dietary carotenoids: studies in mouse and human cells," Pure & Appl. Chem., vol. 66, No. 5, pp. 1025–1032 (1994).
N. Krinsky, "Carotenoids and Cancer: Basic Research Studies," Nat. Antioxid. Health Dis., pp. 239–261 (1994).
J. Bertram, "The chemoprevention of cancer by dietary carotenoids: studies in mouse and human cells," Oxid. Stress and Aging, pp. 221–235 (1995).
Narisawa et al., "Inhibitory effects of natural carotenoids, α–carotene, β–carotene, lycopene and lutein, on colonic aberrant crypt foci formation in rats," Cancer Letters, vol. 107, pp. 137–142 (1996).
Bendich, "Recent Advances in Clinical Research Involving Carotenoids," Pure & Appl. Chem., vol. 66, No. 5, pp. 1017–1024 (1994).
Levy et al., "Lycopene Is a More Potent Inhibitor of Human Cancer Cell Proliferation Than Either α–carotene, β–carotene," Nutr. Cancer, vol. 24, pp. 257–266 (1995).
Giovannucci et al., "Intake of Carotenoids and Retinol in Relation to Risk of Prostate Cancer," J. of Natl. Cancer Inst., vol. 87, No. 23, pp. 1767–1776 (1995).
Khachik et al., "Lutein, Lycopene, and Their Oxidative Metabolites in Chemoprevention of Cancer," J. of Cell. Biochem., Suppl. 22, pp. 236–246 (1995).

Khachik et al., "Partial Synthesis of the Oxidative Metabolites of Lycopene Isolated from Human Serum," 11$^{th}$ International Symposium on Carotenoids, Leiden, The Netherlands, Aug. 18–23 1996.
Khachik et al., "Identification of Carotenoids and their Metabolites in Extracts from Human Plasma, Breastmilk, and Dissected Human Retina," 11$^{th}$ International Symposium on Carotenoids, Leiden, The Netherlands, Aug. 18–23, 1996.
Khachik et al., "Metabolism of Dietary Carotenoids and their Potential Role in Prevention of Cancer and Age–related Macular Degeneration," Book of Abstracts, 213$^{th}$ ACS Nat. Meeting, San Francisco, California, USA, Apr. 13–14, 1997.
Lu et al., "A New Carotenoid, Hydrogen Peroxide Oxidation Products from Lycopene," Biosci. Biotech. Biochem., vol. 59, (11), pp. 2153–2155 (1995).
Hirata et al., "The Stereospecific Hydroxylation of Endocyclic Ethylenic Linkage in the Biotransformation of α–Terpinyl Acetate with Cultured Suspension Cells of Nicotiana Tabacum," Chem. Letters, pp. 671–674 (1982).
Hengartner et al., "Synthesis, Isolation, and NMR–Spectroscopic Characterization of Fourteen (Z)–Isomers of Lycopene and of Some Acetylenic Didehydro– and Tetradehydrolycopenes," Helv. Chim. Acta, vol. 75, pp. 1848–1865 (1992).
Weber et al., "An Improved Procedure for the KMnO$_4$ Oxidation of Olefins to Cis–1,2–Glycols by use of Phase Transfer Catalysis," Tetr. Letters, No. 48, pp. 4907–4908 (1972).
Milas et al., "The Hydroxylation of the Double Bond," J.A.C.S., vol. 58, pp. 1302–1304 (1936).
Koyama et al., "Synthesis of (–) Ambrox from L–Abietic Acid," Tetr. Letters, vol. 28, No. 25, pp. 2863–2866 (1987).
Newhall, "Derivatives of (+)–Limonene.I. Esters of trans–p–Methane–1,2–diol," J. Org. Chem, vol. 23, pp. 1274–1276 (1958).
Viski et al., "A Novel Procedure for the Cleavage of Olefin Derivatives to Aldehydes Using Potassium Permanganate," J. Org. Chem., vol. 51, pp. 3213–3214 (1986).
Meinwald et al., "Synthesis and Sterochemistry of Chrysomelidial and Plagiolactone," J.A.C.S., vol. 100, pp. 1883–1886 (Mar. 15, 1978).
Sakai et al., "Revisions of the Absolute Configurations of C–8 Methyl Groups in Dehydroiridodiol, Neonepetalactone, and Matatabiether from Actinidia Polygama MIQ," Tetrahedron Letters, vol. 36, pp. 3115–3119 (1980).

(List continued on next page.)

*Primary Examiner*—Shailendra Kumar
*Assistant Examiner*—Sreeni Padmanabhan
*Attorney, Agent, or Firm*—Mark E. Waddell; Stephen M. Haracz; Bryan Cave LLP

[57] ABSTRACT

This invention is concerned with the synthesis of 3-(1-acetoxy-1-methylethyl)-6-oxo-heptanal; 3-(1-acetoxy-1-methylethyl)-2-formyl-1-methyl-cyclopentanol; 5-[2-hydroxy-5-(1-hydroxy-1-methylethyl)-2-methyl-2-cyclopentyl]-3-methyl-penta-2,4-dien-1-ol and 2,7,11-trimethyl-13-[2-hydroxy-5-(1-hydroxy-1-methylethyl)-2-methyl-cyclopentyl]-trideca-2,4,6,8,10,12-hexaenal which are useful as intermediates for the synthesis of lycopene metabolites.

4 Claims, No Drawings

OTHER PUBLICATIONS

Wolf et al., "n–Butyl Glyoxylate," Organic Synthesis, vol. IV, pp. 124–125 (1963).

Merrer et al., "Total Synthesis of Leukotriene (+)–LTB$_4$ from D–Mannitol," Tetr. Letters, vol. 27, No. 35, pp. 4161–4164 (1986).

Wolinsky et al., "Synthesis of 4-(2-Methyl-5-isopropenyl-1-cyclopenten-1-yl)butan-2-one," J. Org. Chem., vol. 29, pp. 3740–3742 (1964).

Greene et al., Protective Groups in Organic Synthesis, 2$^{nd}$ Edition, John Wiley & Sons, Inc., New York, pp. 68–83, 1981.

Traber et al., "Synthesis of (all–E,2R,2'R)–Oscillol," Helv. Chim. Acta, vol. 79, pp. 499–506 (1996).

Kienzle et al., "Die Synthese von Actinioerthrol, Violerythrin und anderen 2,2'–Dinorcarotenoiden," Helv. Chim. Acta, vol. 61, Nr. 18, pp. 242–249 (1978).

Haag et al., "Isozeaxanthins: Chiralität und enantioselektive Synthese von 4R,4'R)–Isozeaxanthin ((–)–(4R,4'R)–β,β–Carotin–4,4'–diol)," Helv. Chim. Acta, vol. 65, Nr. 177, pp. 1795–1803 (1982).

Buschor et al., "Synthese der (3S,4R,3'S,4'R)–und (3S,4S, 3'S, 4'S)–Crustaxanthine sowie weiterer verbindungen mit 3,4–Dihydroxy–β–Endgruppen," Helv. Chim. Acta, vol. 73, pp. 1002–1021 (1990).

Organikum, Organisch–chemisches Grundpraktikum, 17$^{th}$ Edition (VEB Deutscher Verlag der Wissenschaften, Berlin), p. 261 (1988).

INTERMEDIATE COMPOUNDS FOR MAKING METABOLITES OF LYCOPENE

This is a divisional of copending application Ser. No. 09/168,143 filed on Oct. 7, 1998.

FIELD OF THE INVENTION

The present invention is concerned with a multi-stage process for the manufacture of an oxidative metabolite of the carotenoid lycopene as well a novel intermediates produced in the manufacturing process.

BACKGROUND OF THE INVENTION

As is known, carotenoids, inter alia, lycopene, play an important role in the chemoprevention (prophylaxis) of cancer [see, for example, J. S. Bertram, Pure & Appl. Chem. 66, 1025–1032 (1994) and the literature references mentioned therein; N. I. Krinsky, Nat. Antioxid. Health Dis. 1994, 239–261; J. S. Bertram, Oxid. Stress Aging 1995, 221–235; as well as T. Narisawa et al., Cancer Lett. 107(1), 137–142 (1996)], and their use in clinical research is well established. [A. Bendich, Pure & Appl. Chem. 66, 1017–1024 (1994) and the literature references mentioned therein]. Levy et al. have demonstrated the preventative activity of lycopene, having the formula against the growth of human endometrial, breast and lung cancer cells [Nutr. Cancer, 24, 257–266 (1995)]. E. Giovannucci et al. disclose in J. Natl. Cancer Inst. 87, 1767–1776 (1995) that a diet rich in lycopene reduces the risk of prostate cancer.

The red carotenoid lycopene is present in tomatoes and among other fruits. A finding that, with respect to the activity against cancer, cooked tomatoes are substantially more active than raw could be due to the fact that after boiling the lycopene has an improved bioavailability; on the other hand, the biologically active compound could be an oxidation product or a metabolite of lycopene. In recent investigations on the carotenoid content of human blood plasma, new lycopene metabolites have been identified, namely 2,6-cyclolycopene-1,5-diol and 5,6-dihydroxy-5,6-dihydrolycopene [F. Khachik et al., J. Cell Biochem. 1995 (Suppl. 22), 236–246 and 11th International Symposium on Carotenoids, Leiden 1996, O.P.1.3; as well as F. Khachik, Book of Abstracts, 213th ACS Nat. Meeting, San Francisco, Apr. 13–14, 1997]. The first-mentioned known metabolite, having the formula

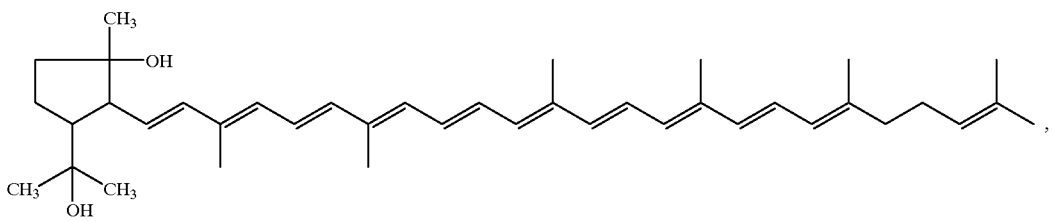

shows activity in and is useful in the prevention of cancer growth in human and mouse cells.

Two syntheses of oxidative metabolites of lycopene have been reported, namely in Biosci. Biotechn. Biochem. 59, 2153–2155 (1995; Y. Lu et al.) and in the aforementioned 11th Int. Symp. on Carotenoids, Leiden 1996 (O.P.3.5; F. Khachik et al.). These are partial syntheses, each of which starts from lycopene itself. It has now been found that 2,6-cyclolycopene-1,5-diol (II) can be made by a multi-stage process, namely starting from the readily available α-terpinyl acetate. This process is the first total synthesis of an oxidatively produced metabolite of lycopene.

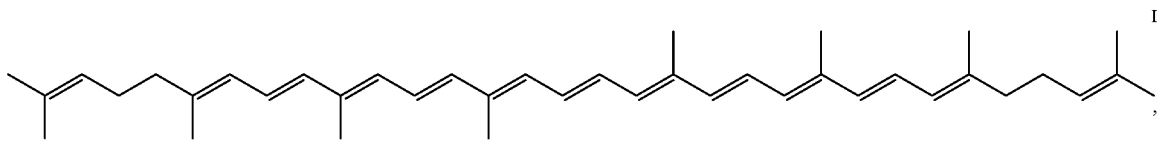

SUMMARY OF THE INVENTION

The invention is accordingly concerned with a process for making the compound of formula II, which comprises the steps of (a) oxidatively dihydroxylating α-terpinyl acetate having the formula

III

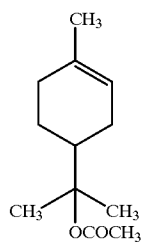

to form 4-(1-acetoxy-1-methylethyl)-1-methyl-cyclohexane-1,2-diol having the formula

IV

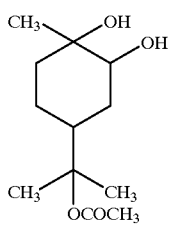

(cyclohexanediol (IV)), (b) oxidatively cleaving the cyclohexanediol (IV) to form 3-(1-acetoxy-1-methylethyl)-6-oxo-heptanal having the formula

V

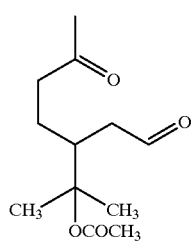

(ketoaldehyde (V)), (c) subjecting the ketoaldehyde (V) to an intramolecular aldol condensation to form 3-(1-acetoxy-1-methylethyl)-2-formyl-1-methyl-cyclopentanol having the formula

VI

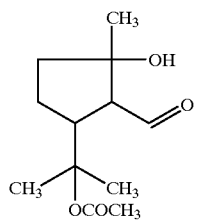

(cyclopentanol (VI)), (d) silylating the cyclopentanol (VI) to form 3-(1-aceotxy-1-methylethyl)-2-formyl-1-methyl-1-trimethylsilyloxy-cyclopentane having the formula

VII

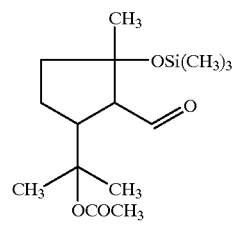

(formylcyclopentane (VII)), (e) subjecting the formylcyclopentane (VII) to a $C_3$-chain lengthening with acetone and simultaneously to a saponification for the cleavage of the acetyl group to form 4-[5-(1-hydroxy-1-methylethyl)-2-methyl-2-trimethylsilyloxy-cyclopentyl]-3-buten-2-one having the formula

VIII

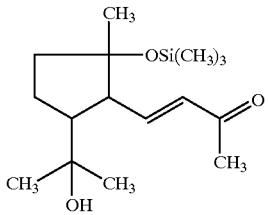

(cyclopenylbutenone (VIII)), (f) reacting the cyclopentylbutenone (VIII) with vinylmagnesium bromide to form 5-[5-(1-hydroxy-1-methylethyl)-2-methyl-2-trimethylsilyloxy-cyclopentyl]-3-methyl-penta-1,4-dien-3-ol having the formula

IX

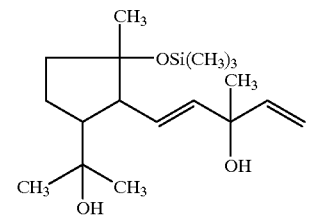

(pentadienol (IX)), (g) converting the pentadienol (IX) with deprotection of the silylated hydroxy group into a (5-[2-hydroxy-5-(1-hydroxy-1-methylethyl)-2-methyl-cyclopentyl]-3-methyl-penta-2,4-dienyl) triphenylphosphonium salt having the formula

X

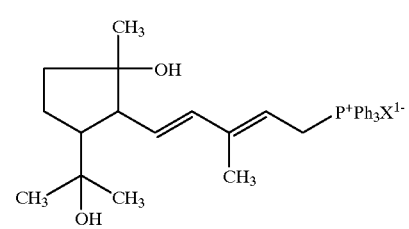

wherein Ph is phenyl and $X^{1-}$ is halide or hydrogen sulphate, (phosphonium salt (X)), (h) subjecting the phosphonium salt (X) to a Wittig reaction with 2,7-dimethyl-2,4,6-octatriene-1,8-dial having the formula

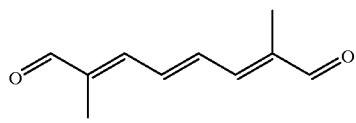

XI ($C_1$-dial (XI)) to form 2,7,11-trimethyl-13-[2-hydroxy-5-(1-hydroxy-1-methylethyl)-2-methyl-cyclopentyl]-trideca-2,4,6,8,10,12-hexaenal having the formula

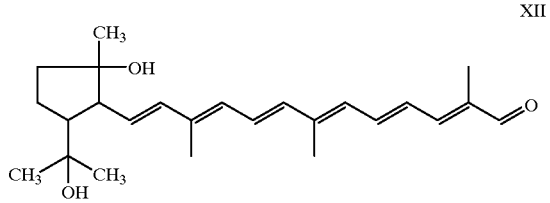

XII (tridecahexaenal (XII)), and (i) subjecting the tridecahexaenal (XII) to a Wittig reaction with a (3,7,11-trimethyl-dodeca-2,4,6,10-tetraenyl)triphenylphosphonium salt having the formula

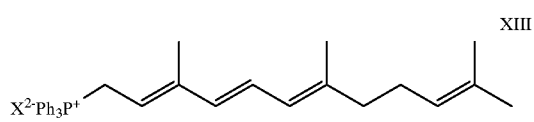

XIII wherein Ph is phenyl and $X^{2-}$ is halide or hydrogen sulphate, (phosphonium salt (XIII)) to form the compound of formula II.

The present invention is concerned with novel intermediates used in the aforementioned process and in particular those intermediates of formulae V, VI, VII, VIII, IX, X and XII. In addition, the present invention is also concerned with the individual process steps IV→V, V→VI, VI→VII, VII→VIII, VIII→IX, IX→X, X+XI→XII and XII+XIII→II, that is, the one-stage processes described above for the production of the novel intermediates and the known final product II. The compounds of formulae III, IV, XI and XIII are known: see, inter alia, T. Hirata et al., Chem. Lett. 1982, 671–674 (cyclohexanediol (IV)) as well as U.S. Pat. No. 5,166,445 and Helv. Chim. Acta 75, 1848–1865 (1992) (phosphonium salt (XIII)).

DETAILED DESCRIPTION OF THE INVENTION

The invention is accordingly concerned with a process making the compound of formula II, which comprises the steps of (a) oxidatively dihydroxylating α-terpinyl acetate having the formula

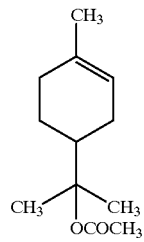

III to form 4-(1-acetoxy-1-methylethyl)-1-methyl-cyclohexane-1,2-diol having the formula

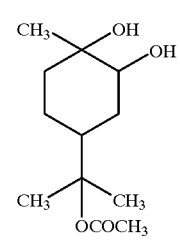

IV (cyclohexanediol (IV)), (b) oxidatively cleaving the cyclohexanediol (IV) to form 3-(1-acetoxy-1-methylethyl)-6-oxo-heptanal having the formula

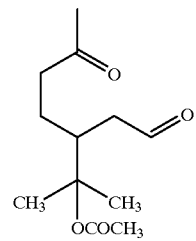

V (ketoaldehyde (V)), (c) subjecting the ketoaldehyde (V) to an intramolecular aldol condensation to form 3-(1-acetoxy-1-methylethyl)-2-formyl-1-methyl-cyclopentanol having the formula

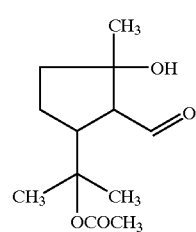

VI (cyclopentanol (VI)), (d) silylating the cyclopentanol (VI) to form 3-(1-acetoxy-1-methylethyl)-2-formyl-1-methyl-1-trimethylsilyloxy-cyclopentane having the formula

VII

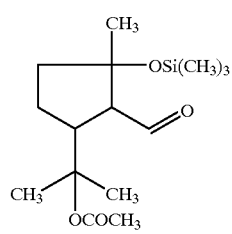

(formylcyclopentane (VII)), (e) subjecting the formylcyclopentane (VII) to a $C_3$-chain lengthening with acetone and simultaneously to a saponification for the cleavage of the acetyl group to form 4-[5-(1-hydroxy-1-methylethyl)-2-methyl-2-trimethylsilyloxy-cyclopentyl]-3-buten-2-one having the formula

VIII

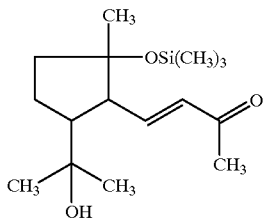

(cyclopentylbutenone (VIII)), (f) reacting the cyclopentylbutenone (VIII) with vinylmagnesium bromide to form 5-[5-(1-hydroxy-1-methylethyl)-2-methyl-2-trimethylsilyloxy-cyclopentyl]-3-methyl-penta-1,4-dien-3-ol having the formula

IX

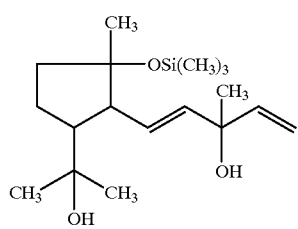

(pentadienol (IX)), (g) converting the pentadienol (IX) with deprotection of the silylated hydroxy group into a (5-[2-hydroxy-5-(1-hydroxy-1-methylethyl)-2-methyl-cyclopentyl]-3-methyl-penta-2,4-dienyl) triphenylphosphonium salt having the formula

X

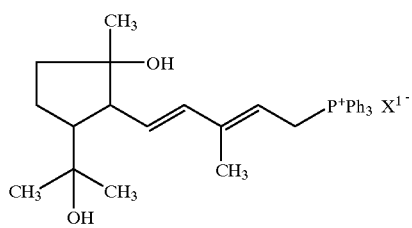

wherein Ph is phenyl and $X^{1-}$ is halide or hydrogen sulphate, (phosphonium salt (X)), (h) subjecting the phosphonium salt (X) to a Wittig reaction with 2,7-dimethyl-2,4,6-octatriene-1,8-dial having the formula

XI

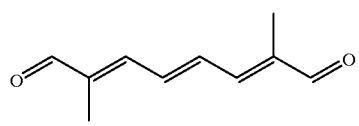

($C_{10}$-dial (XI)) to form 2,7,11-trimethyl-13-[2-hydroxy-5-(1-hydroxy-1-methylethyl)-2-methyl-cyclopentyl]-trideca-2,4,6,8,10,12-hexaenal having the formula

XII

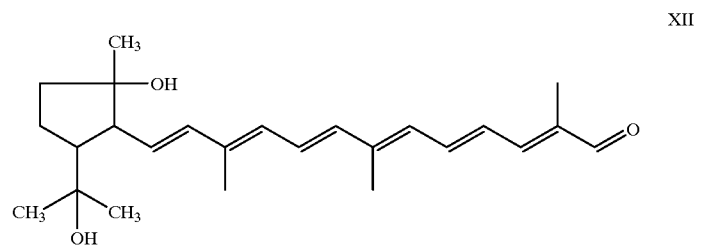

(tridecahexaenal (XII)), and (i) subjecting the tridecahexaenal (XII) to a Wittig reaction with a (3,7,11-trimethyl-dodeca-2,4,6,10-tetraenyl)triphenylphosphonium salt having the formula

XIII

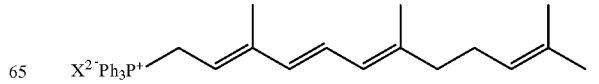

wherein Ph is phenyl and $X^{2-}$ is halide or hydrogen sulphate, (phosphonium salt (XIII)) to form the compound of formula II.

The present invention is concerned with novel intermediates used in the aforementiond process and i particular those intermediates of formulae V, VI, VII, VIII, IX, X and XII. In adition, the present invention is also concerned with the individual process steps IV→V, V→VI, VI→VII, VII→VIII, VIII→IX, IX→X, X+XI→XII and XII+XIII→II, that is, the one-stage processes described above for the production of the novel itnermediates and the known final product II. The compounds of formulae III, IV, XI and XIII are known: see, inter alia, T. Hirata et al., Chem. Lett. 1982, 671–674 (cyclohexanediol (IV)) as well as U.S. Pat. No. 5,166,445 and Helv. Chim. Acta 75, 1848–1865 (1992) (phosphonium salt (XIII)).

A variant of the process in accordance with the present invention described above comprises converting the cyclopentylbutenone (VIII), made by steps (a) through (e) as set forth above, into the phosphonium salt (X) not via the pentadianol (IX), but converting it into the same phosphonium salt (X) via two alternative intermediates; this variant involves three process steps and comprises the steps of subjecting the cyclopentylbutenone (VIII) to a Horner-Emmons olefination with a trialkyl phosphonoacetate in the presence of a base to form the corresponding alkyl 5-[5-(1-hydroxy-1-methylethyl)-2-methyl-2-trimethylsilyloxy-cyclopentyl]-3-methyl-penta-2,4-dienoate having the formula

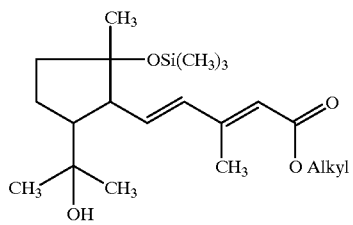

XIV wherein Alkyl is $C_{1-6}$-alkyl,
(pentadienoic acid ester (XIV)), reducing the pentadienoic acid ester (XIV) with deprotection of the silylated hydroxy group to form 5-[2-hydroxy-5-(1-hydroxy-1-methylethyl)-2-methyl-cyclopentyl]-3-methyl-penta-2,4-dien-1-ol having the formula

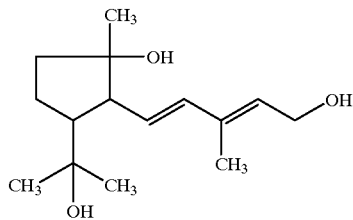

XV (pentadienol (XV)), and converting the pentadienol (XV) into the (5-[2-hydroxy-5-(1-hydroxy-1-methylethyl)-2-methyl-cyclopentyl]-3-methyl-penta-2,4-dinyl) triphenylphosphonium salt of formula X given above (phosphonium salt (X)). The remainder of the multi-stage process for making 2,6-cyclolycopene-1,5-diol, that is, process steps X+XI→XII and XII+XIII→II, is effected as defined and described above. The thus-modified process for making the lycopene metabolite 2,6-cyclolycopene-1,5-diol of formula II starting from α-terpinyl acetate represents a further aspect of the present invention, as do the novel intermediates of formulae XIV and XV produced in the variant as well as the individual processes steps VIII→XIV, XIV→XV and XV→X, that is, the one-stage processe defined above for the production of the novel intermediates.

As used herein, halide refers to fluoride, chloride, bromide, and iodide. Chloride and bromide are preferred with bromide being especially preferred.

As used herein, $C_{1-6}$-alkyl includes, for example, straight and branched chains such as, for example, methyl, ethyl, propyl, isopropyl, butyl, isobutyl, sec-butyl, tert.butyl, pentyl, isopentyl, neopentyl, hexyl, isohexyl, etc.

The oxidative dihydroxylation of α-terpinyl acetate (III) to the cyclohexanediol (IV) is conveniently carried out using the oxidizing agent potassium permanganate in a liquid reaction medium at relatively low temperatures (for example, from about 0° C. to about 40° C.). As the solvent for the α-terpinyl acetate (III) there comes into consideration especially a polar organic solvent, such as an aliphatic or cyclic ether, for example, tetrahydrofuran, or a lower (especially $C_{1-6}$) alkanol, for example, ethanol. The potassium permanganate, in turn, is conveniently dissolved in water, suitably at a concentration in the range of about 2 to about 7% (wt./vol.) and is added slowly in the aqueous solution to the solution of the α-terpinyl acetate. For reasons of safety—and since the reaction generally proceeds well under these conditions—the addition is effected at relatively low temperatures, that is, conveniently in the temperature range of about 0° C. to about 40° C.; because of the danger of an over-oxidation the temperature should be held in the lower part of this range. Conveniently, about 0.8 to about 1.0 equivalent (eq.) of potassium permanganate is used based on the amount of educt. Moreover, during the addition it is advantageous to stir the reaction mixture virorously and it is also suitably stirred further after completion of the addition. In this manner the reaction has normally finished within a maximum of about two hours, with a suspension then being present and the desired cyclohexanediol (IV) being in solution. In order to isolate this product, the suspension is filtered, the filtrate is extracted with a suitable, water-immiscible organic solvent, such as a lower halogenated hydrocarbon, for example, methylene chloride or chloroform, an aliphatic ether, for example, diethyl ether or tert.butyl methyl ether, or a lower aliphatic ester, for example, ethyl acetate, and the organic extraction phase is dried, for example, with anhydrous sodium sulphate for magnesium sulphate, and then evaporated under reduced pressure. If desired, the solid residue can be purified in the usual manner, for example, by recrystallization or column chromatography.

Instead of an aqueous solution of potassium permanganate, this oxidizing agent can be used in another form in the oxidative dihydroxylation; for this there come into consideration, inter alia, potassium permanganate in alkaline solution, especially with aqueous alkali hydroxide solution, for example, aqueous sodium hydroxide or potassium hydroxide solution, and potassium permanganate together with magnesium sulphate in ethanolic-aqueous solution. In both cases the reaction is conveniently effected at low temperatures, for example, in the range of the about 0° C. to about 5° C., whereby in other respects the reaction procedure can be effected in a manner known to those of ordinary skill in the art (see Organikum, page 261, and W. T. Weber et al., Tetr. Lett. 1972, 4907 et seq.). Oxidizing agents other than potassium permanganate come into consideration, especially osmium tetroxide/hydrogen peroxide. In this case, typically a 6–7% solution of hydrogen peroxide in methanol, tert.butanol, acetone or glacial acetic acid and an about 0.5% solution of osmium tetroxide in the same solvent are added to the α-terpinyl acetate (III) and the reaction mixture is stirred for several days. For further details reference is made, for example, to N. A. Milas et al., J.A.C.S. 58, 1302 et seq. (1936).

The conversion of the cyclohexanediol (IV) into the ketoaldehyde (V) is a glycol cleavage as is described, for example, in Tetr. Lett. 28, 2863 et seq. (1987). In the present case IV→V the glycol cleavage is conveniently effected in an aprotic polar or apolar, or even in a protic polar, organic solvent at low to moderate temperatures and using lead (IV) acetate [Pb(OCOCH$_3$)$_4$] as the oxidizing agent. Preferred solvents for this purpose are lower halogenated aliphatic hydrocarbons, for example, methylene chloride; aromatic hydrocarbons, for example, benzene or toluene; or lower aliphatic carboxylic acids, for example, acetic acid. The reaction is suitably effected in the temkperature range of about −20° C. to about 50° C., preferably at about 0° C. The amount of lead (IV) acetate covneniently lies between about 1.0 and about 1.5 equivalents based on the amount of educt. If desired, this agent can be added directly, that is, without dilution, to a solution of the cyclohexanediol (IV) in the chose solvent, or the two reactants can be dissolved or suspended in the solvent, preferably while maintaining a low temperature, especially one which lies below 5° C., and in each case with the exclusion of moisture as far as possible. In order to neutralize the acetic acid which almost inevitably accompanies the lead acetate, the solution or suspension of the cyclohexanediol (IV) is advantageously treated prior to the addition of the lead (IV) acetate with anhydrous sodium carbonate or with another, rather weak, inorganic base; mortared or finely crystalline, anhydrous sodium carbonate is preferably used for this purpose. Moreover, it is advisable to stir the reaction mixture. In this manner the reaction has normally finished within about two hours.

For the working up of the mixture obtained after the reaction, water is suitable added to this mixture and thereby its temperature is left to rise to room temperature. After filtering off residual solid constituents and separating the organic phase containing the product, product remaining in the aqueous phase can be obtained, if desired, by extraction with further organic solvent, for example, methylene chloride. A conventional treatment of the (entire) organic phase (drying over for example, anhydrous sodium sulphate or magnesium sulphate, evaporation and, if desired, purification by column chromatography) yields the desired ketoaldehyde (V).

The next process step is the intramolecular aldol condensation of the ketoaldehyde (V) to the cyclopentanol (VI). This condensation is conveniently carried out by reacting the ketoaldehyde (V) in an organic solvent or even in water at temperatures in the range of about 0° C. to the reflux temperature of the reaction mixture, preferably at temperatures between room temperature and about 50° C., and in the presence of a base and also an organic acid. Suitable organic solvents are primarily lower aliphatic ketones, for example, diethyl ether, tert.butyl, methyl ether or tetrahydrofuran; lower aliphatic ketones, for example, acetone; as well as aromatic hydrocarbons, for example, benzene and toluene. Suitable bases are generally amines, such as, for example, dialkylamines and trialkylamines, and nitrogen-containing heterocyclic compounds, for example, piperidine and pyrrolidine. Acids which come into consideration are, inter alia, lower aliphatic carboxylic acids, for example, acetic acid, and sulphonic acids, for example, p-toluenesulphonic acid.

Both the base and the carboxylic acid can be used in a catalytic amount (up to about 0.02 molar) to about an equimolar amount based on the amount of educt. The condensation has normally finished within a maximum of 100 hours, it being observed that an equilibrium with a product:educt ratio of about 1:1 is achieved at the latest after about 24 hours.

In the case of this intramolecular aldol condensation, the thus-produced cyclopentanol (VI) can be isolated from the reaction mixture and, if desired, purified in a manner known to those of ordinary skill in the art, especially by washing with aqueous basic and/or mineral acidic solution, for example, aqueous sodium carbonate solution, hydrochloric acid solution and/or sodium chloride solution, extraction with a suitable organic solvent, for example with an ether, for example, tert.butyl methyl ether, separation and drying of the organic phase, evaporation of this phase and, if desired, recrystallization and/or purification by column chromatography of the solid residue.

Silylations for the protection of a hydroxyl group are especially familiar reaction steps, inter alia, in the carotenoid field—as in the silylation of the cyclopentanol (VI) to the formylcyclopentane (VII) in the present multi-stage manufacturing process—in relation to which numerous publications exist [see, for example, F. Kienzle and R. E. Minder, Helv. Chim. Acta 61, 242 (1978), A. Haag and C. H. Eugster, ibid. 65, 1795 (1982), as well as D. J. Buschor and C. H. Eugster, ibid. 73, 1002 (1900)]. Not only the trimethylsilyl group, but also other protecting groups are conceivable, provided that they are stable towards enolates and Grignard reagents and are simultaneously acid-stable. Other trialkylsilyl, methoxymethyl, methoxyethoxymethyl and tetrahydropyranyl protecting groups belong to them.

In the present case, it has been found to be convenient to carry out the silyulation (with a trimethylsilyl protecting group) using trimethylchlorosilane as the silylating agent and an aprotic polar organic solvent. Moreover, a base is used as is usual. Suitable solvents are especially lower, halogenated aliphatic hydrocarbons, for example, methylene chloride; nitrogen-containing heterocyclic compounds, for example, pyridine; lower aliphatic and cyclic ethers, for example, diethyl ether or tetrahydrofuran; lower aliphatic amines, for example, triethylamine; and lower aliphatic amides, for example, dimethylformamide. Suitable bases are, inter alia, lower aliphatic amines, for example, triethylamine; aromatic amines, for example, dimethylaniline; and nitrogen-containing, optionally aminated heterocyclic compounds, for example, imidazole and 4-dimethylaminopyridine. As will be evident, the amines can serve not only as solvents, but also as bases. There are conveniently used about 2 to about 4 eq. of trimethylchlorosilane and from about 2 to about 5 eq. of base relative to the amount of educt (based on 1 equivalent).

In practice, the silylation is effected by adding to a solution of the cyclopentanol (VI) and the base in the solvent the silylating agent dissolved in the sanme solvent, and at temperatures in the range of about −10° C. to room temperature (about 25° C.). Moreover, the addition is conveniently effected under an inert protective gas, for example, nitrogen, in order to exclude moisture as far as possible, and with stirring. Under the above conditions the silylation has normally finished within about 24 hours. The working up of the mixture obtained after the reaction can be effected in a conventional manner, for example, by filtering off the solid constituents, evaporating the filtrate and purifying the solid residue, for example by recrystallization and/or column chromatography, in order to obtained more or less pure formylcyclopentane (VII).

The next process step, that is, the $C_3$-chain lengthening with acetone and simultaneous saponification of the formylcyclopentane (VII) to the cyclopentylbutenone (VIII), is conveniently carried out by firstly freshly producing a lithium dialkylamide (as the base) from a lithiumalkyl, for example, n-butyllithium, and a secondary amine, especially a di($C_{1-6}$-alkyl)amine, for example, diisopropylamine, and reacting with acetone in a suitable organic solvent, especially an aprotic polar solvent, to give the acetone enolate; then the enolate is reacted with the formylcyclopentane (VII). A suitable organic solvent for the "in situ" lithium dialkylamide production is generally an aprotic solvent, such as a lower aliphatic or cyclic ether, for example, diethyl ether or tetrahydrofuran, or an aromatic hydrocarbon, for example, toluene. This production is, moreover, conveniently effected at relatively low temperatures, especially in the range of about –10° C. to about +10° C., preferably at about 0° C., under an inert protective gas, for example, nitrogen, and while stirring. The lithiumalkyl and the secondary amine are suitably used in about equimolar amounts. After a sufficient reaction period, which is normally up to about one hour, the mixture is conveniently cooled to about –70° C. and subsequently the acetone is added in the same solvent. Conveniently, a clear excess of the lithium dialkylamide base, especially about 1.1 to about 2 equivalents, is used relative to the acetone (1 eq.) in order to suppress the self-condensation of the acetone as far as possible. After a brief period of stirring at the low temperature the formylcyclopentane (VII) is added, conveniently in a somewhat lower molar amount than the amount of acetone. While warming the reaction mixture to about –20° C. to about 0° C. the acetone reacts with the formylcyclopentane (VII), and relatively rapidly in the mentioned temperature range. For the isolation and purification of the thus-produced cyclopentylbutenone (VIII), the mixture can be trated, for example, with saturated aqueous ammonium chloride solution, the organic phase separated and washed with water and/or saturated aqueous sodium chloride solution, dried over a drying agent, such as, for example anhydrous sodium sulphate or magnesium sulphate and the organic phase finally evaporated; if desired further purification of the residue obtained can be undertaken for example by recrystallization and/or column chromatography.

The subsequent stage of the process is a Grignard reaction. The cyclopentylbutenone (VIII) and the vinylmagnesium bromide are conveniently reacted with one another in an aprotic, polar, organic solvent, such as a lower aliphatic or cyclic ether, for example, diethyl ether or dimethoxyethane or, respectively, tetrahydrofuran, tetrahydropyran or dioxan, or an amide, for example, hexamethyl phosphortriamide, and in a temperature range of about –50° C. to about 0° C., preferably of about –40° C. to about –20° C. Conveniently, about 2 to 4 equivalents of vinylmagnesium bromide are used per equivalent of cyclopentylbutanone (VIII). The addition of an aliphatic amine, for example, triethylamine, serves to increase the activity. The isolation and purification of the thus-obtained pentadienol (IX) can be carried out analogously to the procedure described in connection with the foregoing process step VII→VIII.

As an additional embodiment in the process in accordance with the invention, the free tertiary hydroxyl group of the cyclopentylbutenone (VIII) can be protected immediately prior to process step VIII→VII, conveniently by rimethylsilylation analogously to process step VI→VII; after the correspondingly modified process step VIII→IX the silylated hydroxyl group can be deprotected in a conventional manner, which again yields the pentadienol (IX).

The subsequent phosphonium salt formation IX→X is conveniently carried out by stirring a solution of the pentadienol (IX) and a triphenylphosphonium halide or triphenylphosphonium hydrogen sulphate in a polar organic solvent for several hours. Lower aliphatic alcohols, for example, methanol and ethanol; and lower halogenated aliphatic hydrocarbons, for example, methylene chloride and chloroform, are especially suitable as such solvents. Suitable, between about 1 and about 1.2 equivalents or triphenylphosphonium halide or hydrogen sulphate are used per equivalent of pentadienol (IX). This triphenylphosphonium salt is preferably a halide, especially the chloride or bromide, with triphenylphosphonium bromide being particular preferred. The reaction is conveniently carried out in the temperature range of about 0° C. to about 50° C., preferably at room temperature, and as a rule takes from about 12 to about 72 hours. The isolation and—where desired—purification of the thus-obtained phosphonium salt (X) can be carried out according to methods known to those of ordinary skill in the art.

The penultimate process stage and the final process stage of the multi-stage manufacturing process in accordance with the invention are in each case a Wittig reaction which is well-known, especially in carotenoid chemistry. In both cases similar reaction conditions can be used, with in general more drastic conditions, inter alia higher temperatures, being possible for the final process step. The two reactants are each conveniently reacted with one another in a protic or aprotic polar organic solvent in the presence of a base. As such solvents there come into consideration especially lower aliphatic alcohols, for example, methanol and ethanol; lower halogenated aliphatic hydrocarbons, for example, methylene chloride and chloroform; alicyclic ethers, for example, epoxybutane and other oxiranes, and tetrahydrofuran; dimethylformamide; and dimethyl sulphoxide.

The reaction is effected in the first case (X+XI→XII) conveniently at temperatures in the range of about 0° C. to aobut 60° C., preferably at room temperature, and in the second case (XII+XIII→II) conveniently at temperatures in the range of about 0° C. to about 60° C., preferably at about 40° C. Moreover, it is advisable to use the respective phosphonium salt (X) or (XIII) in a slight excess, suitably in up to about 10 percent excess. The working up is conveniently effected by partitioning the mixture obtained after the reaction between water and an aprotic, polar organic solvent, such as a lower aliphatic ether, ester or halogenated hydrocarbon, for example, diethyl ether, ethyl acetate or, respectively, methylene chloride or chloroform, separating the organic phase, washing this with saturated sodium chloride solution, extracting the aqueous phase with further organic solvent, drying the combined organic phases, for example with anhydrous sodium sulphate or magnesium sulphate, evaporating the organic phase, which is dried and freed from drying agent, and purifying the thus-obtained solid, for example, by column chromatography and/or recrystallization.

After column chromatography, the compounds XII and II are normally each obtained as an E/Z isomer mixture from which the (all E)-isomer can be isolated by recrystallization, for example, from hexane. In general, the isomerism of the respective product obtained can, if desired, be controlled in the overall multi-stage process. Thus, starting from (4R)-α-terpinyl acetate of formula III ((4R)-III) there can be produced in sequence (1RS,2RS,4R)-IV, (3R)-V, (1R,2S,3R)-VI, (1R,2S,3R)-VII, (1'R,2'S,3'R)-VIII, (1'R,2'S,3'R,3RS)-IX, (1'R,2'S,3'R)-X, (1'R,2'S,3'R)-XII and (all-E,2R,5R,6S)-II. The corresponding enantiomers can be produced from (4S)-α-terpinyl acetate.

A variant of the process in accordance with the present invention described above comprises converting the cyclopentylbutenone (VIII) into the phosphonium salt (X) not via the pentadianol (IX), but converting it into the same phosphonium salt (X) via two alternative intermediates; this variant involves three process steps and comprises the steps of subjecting the cyclopentylbutenone (VIII) to a Horner-Emmons olefination with a trialkyl phosphonoacetate in the presence of a base to form the corresponding alkyl 5-[5-(1-hydroxy-1-methylethyl)-2-methyl-2-trimethylsilyloxy-cyclopentyl]-3-methyl-penta-2,4-dienoate having the formula

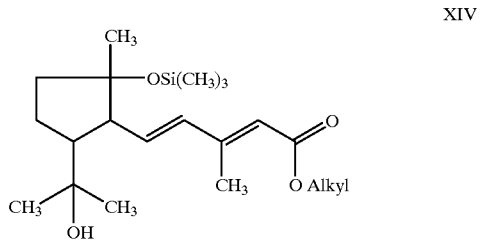

XIV wherein Alkyl is $C_{1-6}$-alkyl,
(pentadienoic acid ester (XIV)), reducing the pentadienoic acid ester (XIV) with deprotection of the silylated hydroxy group to form 5-[2-hydroxy-5-(1-hydroxy-1-methylethyl)-2-methyl-cyclopentyl]-3-methyl-penta-2,4-dien-1-ol having the formula

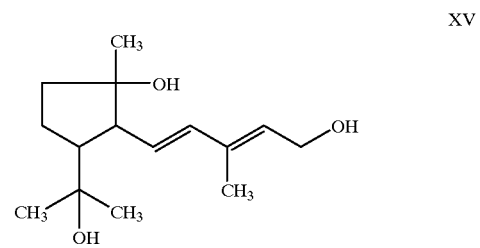

XV (pentadienol (XV)), and converting the pentadienol (XV) into the (5-[2-hydroxy-5-(1-hydroxy-1-methylethyl)-2-methyl-cyclopentyl]-3-methyl-penta-2,4-dienyl) triphenylphosphonium salt of formula X given about [phosphonium salt (X)]. The remainder of the multi-stage process for making 2,6-cyclolycopene-1,5-diol, that is, process steps X+XI→XII and XII+XII→II, is effected as defined and described above. The thus-modified process for making the lycopene metabolite 2,6-cyclolycopene-1,5-diol of formula II starting from α-terpinyl acetate represents a further aspect of the present invention, as do the novel intermediates of formulae XIV and XV produced in the variant as well as the individual processes steps VIII→XIV, XIV→XV and XV→X, that is, the one-stage processes defined above for the production of the novel intermediates.

The reaction of the cyclopentylbutenone (VIII) with the trialkyl phosphonoacetate (Horner-Emmons olefination) is conveniently effected in a lower aliphatic ether or diether for example, dimethoxyethane, as the solvent and in the presence of a strong base, especially an alkali metal hydride, for example, sodium hydride; an alkali metal alkoxide, for example, sodium methoxide or ethoxide; an alkyllithium, for example, butyllithium; or a lithium dialkylamide, for example, lithium diisopropylamide. The reaction is effected at low temperatures, namely at temperatures below about −10° C.; the lower limit lies at about −60° C. It has been found to be practical to add a cooled solution of the trialkyl phosphonoacetate slowly to a likewise cooled suspension of the strong base in the same solvent while stirring and cooling and, after a period of stirring, also to add a solution of the cyclopentylbutenone (VIII) in the same solvent, with the temperature of the respective mixture always being held below about −10° C. Moreover, it is recommended to carry out these operations under an inert gas, for example, nitrogen or argon. Finally, the reaction mixture is stirred for several hours, for examkple 5 to 15 hours, and gradually left to warm to room temperature. The isolation and purification of the thus-obtained pentadienoic acid ester (XIV) can be carried out analogously to the procedure described in connection with process step VII→VIII, although after the treatment with saturated aqueous ammonium chloride solution and prior to the separation of the organic phase an additional organic solvent for example, ethyl acetate, is suitably added for extraction.

The subsequent step of this process variant comprises the reduction of the ester group -COOAlkyl of the pentadienoic acid ester (XIV) as well as the deprotection of the likewise present trimethylsilyloxy group. The reduction is conveniently carried out using a reducing agent conventionally employed for this purpose, especially a metal hydride, for example, diisobutyl aluminium hydride or lithium aluminium hydride, or an alkoxy-metal hydride. Moreover, the reaction is conveniently effected in an aliphatic hydrocarbon, for example, hexane; an aliphatic or cyclic ether, for example, diethyl ether or tetrahydrofuran, a lower aliphatic alocohol, for example, ethanol, or another water-soluble organic solvent at temperatures which are generally low. When diisobutylaluminium hydride is used as the reducing agent, the reaction is effected, for example, at temperatures which do not exceed a maximum of about −40° C. and which as a rule lie at about −60° C. After treatment of the pentadienoic acid ester (XIV) with the reducing agent, the reaction mixture can, however, be left to warm to room temperature, and subsequently the work up can also be carried out analogously to the procedure described in connection with the above described process step VII→VIII with an included extraction step using, for example, ethyl acetate as the extracting agent, whereby in comparison to the work up according to the foregoing process step VIII→XIV the evaporated organic phase is also treated with an organic or inorganic acid as an aqueous solution, for example, hydrochloric acid (which brings about the deprotection). This acid treatment is then conveniently followed by a partition of the mixture between water and the extracting agent, drying and evaporation of the (combined) organic phase(s) and, if desired, also further purification, for example, by recrystallization and/or column chromatography.

The subsequent phosphonium salt formation XV→X can be carried out analogously to the phosphonium salt formation IX→X described above, that is, the equivalent reaction conditiosn apply to this reaction.

As mentioned above, the present invention is also concerned with novel intermediates produced in the manufacturing process (in both variants), that is, 3-(1-acetoxy-1-methylethyl)-6-oxo-heptanal of formula V,
3-(1-acetoxy-1-methylethyl)-2-formyl-1-methyl-cyclopentanol of formula VI,
3-(1-acetoxy-1-methylethyl)-2-formyl-1-methyl-1-trimethylsilyloxy-cyclopentane of formula VII,
4-[5-(1-hydroxy-1-methylethyl)-2-methyl-2-trimethylsilyloxy-cyclopentyl]-3-buten-2-one of formula VIII, 5-[5-(1-hydroxy-1-methylethyl)-2-methyl-2-trimethylsilyloxy-cyclopentyl]-3-methyl-penta-1,4-dien-3-ol of formula IX,
(5-[2-hydroxy-5-(1-hydroxy-1-methylethyl)-2-methyl-cyclopentyl]-3-methyl-penta-2,4-dienyl) triphenylphosphonium salt of formula

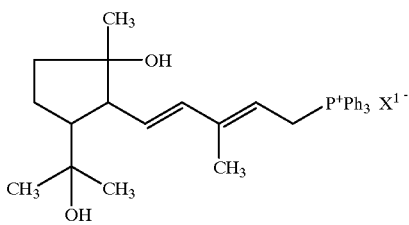

X wherein Ph is phenyl and $X^{1-}$ is halide or hydrogen sulphate,
2,7,11-trimethyl-13-[2-hydroxy-5-(1-hydroxy-1-methylethyl)-2-methyl-cyclopentyl]-trideca-2,4,6,8,10,12-hexaenal of formula XII,
alkyl 5-[5-(1-hydroxy-1-methylethyl)-2-methyl-2-trimethylsilyloxy-cyclopentyl]-3-methyl-penta-2,4-dienoates of formula

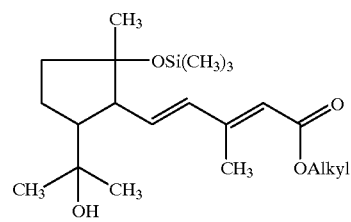

XIV wherein Alkyl is $C_{1-6}$-alkyl,
as well as
5-[2-hydroxy-5-(1-hydroxy-1-methylethyl)-2-methyl-cyclopentyl]-3-methyl-penta-2,4-dien-1-ol of formula XV,
in each case as the racemate or in the respective optically active form given above, which can be produced starting from (4R)- or (4S)-α-terpinyl acetate.

The present invention is illustrated by the following Examples.

EXAMPLE 1

Oxidative Dihydroxylation III→IV

A solution of 50 g (255 mmol) of α-terpinyl acetate in 800 ml of tetrahydrofuran was cooled to 0° C. A solution of 50 g (316 mmol) of potassium permanganate in 1 l of water was added dropwise within 2 hours while stirring vigorously and, after removal of the cooling, the reaction mixture was stirred for a further hour. Then, the mixture was filtered through Celite® (filter aid consisting of kieselguhr (amorphous silica or diatomaceous earth) of various particle sizes) and the filtrate was extracted with ethyl acetate. The organic phase was dried over anhydrous magnesium sulphate and subsequently evaporated under reduced pressure. The residue was recrystallized from the minimum amount of ethyl acetate and added hexane at 4° C. and, in order to obtain additional product, the mother liquor was purified by column chromatography using silica gel and a hexane/ethyl acetate mixture (1:1) and the residue obtained therefrom by evaporation was recrystallized in the same manner. The total yield of thus-obtained 4-(1-acetoxy-1-methylethyl)-1-methyl-cyclohexane-1,2-diol, m.p. 88° C., as white needles was 33.77 g (148 mmol; 65% of the theoretical yield; 5.38 g of educt were recovered).

$^1$H—NMR (300 MHz, CDCl$_3$): 3.36 [dd, J=11.4;4.4, H—C(2)]; 2.3 [br.s., 2× OH]; 2.01 [m, H—C(4)]; 1.94 [s, CH$_3$COO]; 1.81 [dm, J=11.4, H—C(5)]; 1.67 [dm, J=11.4, H—C(3)]; 1.40 [m, H$_2$—C(6); 1.39 [s, H$_3$C(9)]; 1.38 [s, H$_3$C(10)]; 1.36 [m, H—C(3)]; 1.28 [m, H—C(5)]; 1.23 [H$_3$C(7)].

$^{13}$C—NMR (75.5 MHz, CDCl$_3$): 170.57 [C=O]; 84.55 [C(8)]; 75.13 [C(2)]; 70.71 [C(1)]; 44.35 [C(4)]; 37.03 [C(5)]; 31.27 [C(3)]; 27.07 [C(7)]; 23.58 [C(9)]; 23.34 [C(10)]; 22.45 [CH$_3$CO]; 21.68 [C(6)].

IR (CHCl$_3$): 3620 w, 3570 w, 300 m, 2930 m, 1715 s, 1420 w, 1365 s, 1270 s, 1150 m, 1115 m, 1035 m, 1010 m.

MS (EI, 70 eV, 250° C.): 215 (1, M+/−15), 197 (3), 187 (3), 170 (62), 152 (50), 137 (43), 126 (100), 111 (73), 108 (84), 93 (48), 71 (55), 59 (24), 43 (58).

Starting from optically active (R)-α-terpinyl acetate there is obtained in the above manner the cyclohexanediol (IV) as a 1RS, 2RS, 4R-diastereomer mixture; $[\alpha]_D^{23}$: −3.3° (c=0.04 in CH$_3$OH).

EXAMPLE 2

Oxidative Cleavage IV→V 33.77 g (148 mol) of 4-(1-acetoxy-1-methylethyl)-1-methylcyclohexane-1,2-diol and 34.88 g (327 mmol) of anhydrous, finely mortared sodium carbonate were placed in 1 l of methylene chloride and the mixture was cooled to 0° C. Then, 93.3 g of an 85:15 mixture of lead(IV) acetate (156 mol) and acetic acid were added portionwise to the mixture in such a manner that the temperature did not rise above 6° C. The mixture was stirred for one hour, treated with 50 ml of water and warmed to room temperature. Subsequently, the aqueous-organic mixture was filtered through Celite®, the organic phase was separated from the filtrate, the aqueous phase was extracted with methylene chloride, the combined organic phases were dried over anhydrous magnesium sulphate, the dried organic phase was evaporated under reduced pressure and the residue was purified by column chromatography using silica gel as the stationary phase and a 3:2 mixture of hexane and ethyl acetate as the eluting agent.

In this manner there were obtained 30.14 g (133 mmol) of 3-(1-acetoxy-1-methylethyl)-6-oxo-heptanal as a white was, m.p. 24° C.; the yield was 90% of theory.

$^1$H—NMR (300 MHz, CDCl$_3$): 9.72 [dd, J=2.5;1,8, H—C(1)]; 2.58 [ddd, J=16.9;5.8;2.5, H—C(2)]; 2.46 [m, H$_2$—C(5)]; 2.44 [m, H—C(3)]; 2.26 [ddd, J=16.9;5.8;1.8, H—C(2)]; 2.13 [s, H$_3$C(7)]; 1.93 [s, CH$_3$COO]; 1.84 [m, H—C(4)]; 1.53 [s, H$_3$C(2')]; 1.42 [s, H$_3$C—C(1')]; 1.37 [m, H—C(4)].

$^{13}$C—NMR (75.5 MHz, CDCl$_3$): 207.89 [C(6)]; 201.62 [C(1)]; 170.12 [C=O]; 84.40 [C(1')]; 44.96 [C(2)]; 41.99 [C(5)]; 41.88 [C(3)]; 30.04 [C(7)]; 24.17 [C(4)]; 24.15 [C(2')]; 22.39 [CH$_3$COO]; 22.02 [CH$_3$—C(1')].

IR (CHCl$_3$): 3020 m, 2810 w, 2720 w, 1720 s, 1370 s, 1260 s, 1135 m, 1015 m. MS (EI, 70 eV, 150° C.): 228 (1,M$^+$); 169 (23); 154 (40); 122 (47); 110 (100); 101 (32); 95 (41); 81 (89), 70 (38); 59 (35); 43 (95).

Starting from the 1RS,2RS,4R-diastereoisomer mixture of the cyclohexanediol (IV) there is obtained in the above manner the ketoaldehyde (V) as the 3R-isomer, $[\alpha]_D^{23}$ −6.3° (c=0.28 in CH$_3$OH).

EXAMPLE 3

Intramolecular Aldol Condensation V→VI 11.59 g (51.1 mmol) of 3-(1-acetoxy-1-methylethyl)-6-oxo-heptanal were dissolved in 250 ml of tetrahydrofuran together with 2.3 ml of piperidine, 2.3 ml of acetic acid and 1.15 ml of water, and the solution was stirred at room temperature for 21.5 hours. The solution was then washed in sequence with 5% sodium carbonate solution, with 2N hydrochloric acid and with saturated sodium chloride solution and the aqueous phases were each extracted with tert.butyl methyl ether. The combined organic phases were dried with anhydrous magnesium sulphate and evaporated under reduced pressure, and the residue was then purified by column chromatography using silica gel as the stationary phase and a 13:7 mixture of hexane and ethyl acetate as the eluting agent.

In this manner there were obtained 5.26 g (23.1 mmol) of 3-(1-acetoxy-1-methylethyl)-2-formyl-1-methyl-cyclopentanol as a colourless oil. The yield was 45% of theory; as 4.76 g (20.9 mmol, 41%) of the educt used were recovered, the yield of product was 77% based on the conversion.

$^1$H—NMR (300 MHz, CDCl$_3$): 9.78 [d, J=3.3, HC=O]; 3.04 [td, J=9.9;6.2,H—C(3)]; 2.51 [dd, J=9.9;3.3,H—C(2)]; 2.15–1.96 [m, H—C(4)]; 1.92 [s, CH$_3$COO]; 1.84–1.52 [m, H—C(4), H$_2$—C(5)]; 1.48 [s, H$_3$C(2')]; 1.46 [s, H$_3$C—C(1)]; 1.45 [s, H$_3$C—C(1')].
$^{13}$C—NMR (75.5 MHz, CDCl$_3$): 205.5 [HC=O]; 170.2 [O—C=O]; 83.6 [C(1)]; 83.0 [C(1')]; 61.7 [C(2)]; 50.4 [C(3)]; 41.7 [C(4)]; 27.4 [C(2')]; 25.0 [CH$_3$—C(1')]; 24.9 [C(5)]; 21.8 [CH$_3$—C(1)], 22.2 [CH$_3$COO].
IR (CHCl$_3$): 3610 w, 3000 m, 1720 s, 1460 w, 1375 m, 1270 s, 1215 s, 1130 m, 1020 w.
MS (EI, 70 eV, 240° C.): 228 (1, M$^+$); 168 (19); 153 (32); 123 (37); 110 (92); 95 (42); 81 (87); 69 (29); 59 (30); 43 (100).

Starting from the 3R-isomer of the ketoaldehyde (V) there is obtained in the above manner the cyclopentanol (VI) as the 1R,2S,3R-isomer, $[\alpha]^{24}_D$: −4.3° (c=0.38 in CH$_3$OH).

EXAMPLE 4

Silylation VI→VII 620 mg (2.72 mmol) of 3-(1-acetoxy-1-methylethyl)-2-formyl-1-methyl-cyclopentanol and 600 mg (7.5 mmol) of imidazole were dissolved in 10 ml of methylene chloride and a solutio of 0.45 ml (3.56 mmol) of trimethylchlorosilane in 5 ml of methylene chloride was sprayed into the solution at room temperature. The reaction mixture was stirred at this temperature under nitrogen for 17 hours. For the working up, the mixture was filtered, the filtrate was evaporated under reduced pressure and the residue was purified by column chromatography using silica gel and a 17:3 mixture of hexane and ethyl acetate.

In this manner there were obtained 490 mg (1.63 mmol; 60% of the theoretical yield) of 3-(1-acetoxy-1-methylethyl)-2-formyl-1-methyl-5-trimethylsilyloxy-cyclopentane as a white wax.
$^1$H—NMR (300 MHz, CDCl$_3$): 9.45 [d, J=5, HC=O]; 2.93 [td, J=9.3;6.9, H—C(3)]; 2.19 [dd, J=9.3;4.2, H—C(2)]; 1.95–1.85 [m, H—C(4)]; 1.77 [s, CH$_3$COO]; 1.59–1.42 [m, H—C(4), H$_2$—C(5)]; 1.33 [s, H$_3$C(2')]; 1.32 [s, H$_3$C—C(1)]; 1.30 [s, H$_3$C—C(1')]; −0.02 [s, (CH$_3$)$_3$Si].
$^{13}$C—NMR (75.5 MHz, CDCl$_3$): 205.1 (HC=O); 170.0 (O—C=O); 86.0 [C(1)]; 83.3 [C(1')]; 63.1 [C(2)]; 48.9 [C(3)]; 41.4 [C(4)]; 27.1 [C(2')]; 24.9 [C(5)]; 24.6 [CH$_3$—C(1')]; 22.0 [CH$_3$—C(1)]; 21.8 [CH$_3$COO]; 1.8 [(CH$_3$)$_3$Si].
IR (CHCl$_3$): 2990 m, 1725 s, 1460 w, 1380 m, 1265 s, 1215 s, 1140 m, 1045 m.
MS (EI, 70 eV, 150° C.): 240 (39); 225 (100); 197 (20); 143 (92); 133 (36); 122 (65 ); 81 (47); 73 (51); 43 (41).

Starting from the 1R,2S,3R-isomer of the cyclopentanol (VI) there is obtained in the above manner the formylcyclopentane (VII) as the 1R,2S,3R-isomer, $[\alpha]^{20}_D$: −12° C. (d=0.076 in CH$_3$OH).

EXAMPLE 5

C$_3$-chain Lengthening and Saponification VII→VIII

275 μl (2 mmol) of diisopropylamine were placed in 8 ml of tetrahydrofuran and 1.25 ml of butyllithium (2 mmol, 1.6M in hexane) were sprayed in under nitrogen at 0° C. The mixture was stirred for 30 minutes, cooled to −70° C. and 110 μl (1.5 mmol) of actone in 1 ml of tetrahydrofuran was sprayed in. The resulting solution of lithium diisopropylamide was stirred for 15 minutes and thereafter 300 mg (1 mmol) of 3-(1-acetoxy-1-methylethyl)-2-formyl-1-methyl-1-trimethylsilyloxy-cyclopentane in 1.5 ml of tetrahydrofuran were sprayed in. The reaction mixture was warmed to 0° C. within 2 hours and subsequently treated cautiously with 10 ml of saturated ammonium chloride solution. The organic phase was separated, washed with water and saturated sodium chloride solution, dried with anhydrous magnesium sulphate and finally evaporated under reduced pressure. Purification of the residue was effected as usual by column chromatography using silica gel and a 3:1 mixture of hexane and ethyl acetate.

In this manner there were obtained 210 mg (0.7 mmol; 70% of the theoretical yield) of 4-[5-(1-hydroxy-1-methylethyl)-2-methyl-2-trimethylsilyloxy-cyclopentyl]-3-buten-2-one as a colourless oil.
$^1$H—NMR (300 MHz, CDCl$_3$): 6.83 [dd, J=16.2;9.6, H—C(4)]; 6.01 [d, J=16.2, H—C(3)]; 2.33 [td, J=9.9;5.9, H—C(3')]; 2.21 [s, H$_3$C(1)]; 2.16 [t, J=9.6, H—C(2')]; 1.98 [m, H—C(4'α)]; 1.83 [m, H—C(5'α)]; 1.61 [m, H—C(4'β), H—C(5'β)]; 1.25 [s, H$_3$C(2")]; 1.16 [s, H$_3$C-(1')]; 1.14 [s, H$_3$C—C(1")]; 0.08 [(H$_3$C)$_3$Si].
$^{13}$C—NMR (75.5 MHz, CDCl$_3$): 198.7 [C(2)]; 152.5 [C(4)]; 132.3 [C(3)]; 85.8 [C(1')]; 72.9 [C(1")]; 56.9 [C(2')]; 54.4 [C(3')]; 40.7 [C(5')]; 28.5 [C(2")]; 27.8 [CH$_3$—C(1')]; 26.2 [C(1)]; 26.0 [CH$_3$—C(1")]; 25.4 [C(4')]; 2.2 [(CH$_3$)$_3$Si].
IR (CHCl$_3$): 3440 w, 2980 s, 2375 w, 1730 w, 1675 s, 1620 m, 1385 m, 1255 s, 1050 m, 860 s.
MS (EI, 70 eV, 150° C.): 298 (2, M$^+$); 280 (25); 265 (16); 240 (31); 227 (28); 208 (42); 193 (29); 182 (30); 143 (100); 101 (62); 73 (50); 59 (54); 43 (56).

Starting from the 1R,2S,3R-isomer of the formylcyclopentane (VII) there is obtained in the above manner the cyclopentylbutenone (VIII) as the 1'R,2'S,3'R-isomer, $[\alpha]^{22}_D$: −116° C. (c=0.324 in CH$_3$OH).

EXAMPLE 6

Grignard Reaction VIII→IX 6.6 ml (6.6 mmol) of a 1M solution of vinylmagnesium bromide in diethyl ether were dissolved in 30 ml of tetrahydrofuran and the solution was then cooled to −50 ° C. under nitrogen. Subsequently, a solution of 490 mg (1.64 mmol) of 4-[5-(1-hydroxy-1-methylethyl)-2-methyl-2-trimethylsilyloxy-cyclopentyl]-3-buten-2-one in 10 ml of tetrahydrofuran was slowly sprayed in, the reaction mixture was stirred for 30 minutes, a further 3 ml of the ethereal solution of vinylmagnesium bromide (3 mmol $CH_2$=CHMgBr) were added and the mixture was warmed to 0° C.

For the working up, the mixtuer was treated with 20 ml of saturated ammonium chloride solution, the organic phase was separated, washed with sodium chloride solution, dried with anhydrous magnesium sulphate and evaporated under reduced pressure. Purification of the residue was effected as usual by column chromatography using silica gel and a 17:8 mixture of hexane and ethyl acetate.

In this manner there were obtained 190 mg (0.58 mmol, 35% of the theoretical yield) of 5-[5-(1-hydroxy-1-methylethyl)-2-methyl-2-trimethylsilyloxy-cyclopentyl]-3-methyl-penta-1,4-dien-3-ol as a colourless oil.

$^1$H—NMR (300 MHz, $CDCl_3$): 5.91 [dd, J=17.3;10.7, H—C(2)]; 5.65 [dd, J=15.8;8.8, H—C(5)]; 5.53 [d, J=15.8; H—C(4)]; 5.18 [dd, J=17.3;1.1, H—C(1)]; 4.98 [dd, J=10.7;1.1, H—C(1)]; 2.96 [br.s, 2 OH]; 2.19 [m, H—C(3')]; 1.90 [m, H—C(2')]; 1.81 [m, H—C(4'α)]; 1.73 [m, H—C(5'α)]; 1.49 [m, H—C(5'β)]; 1.38 [m, H—C(4'β)]; 1.34 [s, $H_3$C—C(3)]; 1.17 [s, $H_3$C—C(1')]; 1.10 [s, $H_3$C(2"), $H_3$C—C(1")]; 0.08 [s, $(H_3C)_3$—Si].

$^{13}$C—NMR (75.5 MHz, $CDCl_3$): 144.3 [C(2)]; 137.5 [C(4)]; 131.3 [C(5)]; 112.0 [C(3)]; 111.7 [C(1)]; 84.6 [C(1')]; 73.0 [C(1")]; 56.5 [C(2')]; 53.8 [C(3')]; 40.2 [C(5')]; 28.5 [C(2")]; 27.5 [Me—C(3)]; 26.6 [Me—C(1")]; 25.8 [Me—C(1')]; 25.1 [C(4')]; 2.2 [$(CH_3)_3$Si].

IR (NaCl): 3400 s, 3040 w, 2970 s, 1620 w, 1455 m, 1380 s, 1245 s, 1095 s, 1040 s, 835 s.

MS (EI, 70 eV, 80° C.): 326 (1, M$^+$); 308 (28); 293 (13); 241 (40); 223 (89); 218 (72); 197 (37); 173 (81); 143 (100); 117 (28); 73 (53); 57 (23); 43 (44).

Starting from the 1'R,2'S,3'R-isomer of the cyclopentyl-butenone (VIII) there is obtained in the above manner the pentadienol (IX) as a 1'R,2'S,3'R,3RS-isomer mixture, $[\alpha]^{25}_D$: −85° (c=0.355 in $CH_3OH$).

EXAMPLE 7

Deprotection and Phosphonium Salt Formation
IX→X 520 mg (1.6 mmol) of 5-[5-(1-hydroxy-1-methylethyl)-2-methyl-2-trimethylsilyloxy-cyclopentyl]-3-methyl-penta-1,4-dien-3-ol and 600 mg (1.75 mmol) of triphenylphosphonium bromide were dissolved in 16 ml of a 1:1 mixture of methanol and chloroform and the solution was stirred for 23 hours at room temperature under nitrogen and with the exclusion of light. Thereafter, the mixture was evaporated and the residue, dissolved in a small amount of methylene chloride, was precipitated in ice-cold tert.butyl methyl ether. After decanting off the supernatant and filtration the collected precipitate was washed with tert.butyl methyl ether and dried under reduced pressure.

In this manner there were obtained 1.09 g of crude (5-[2-hydroxy-5-(1-hydroxy-1-methylethyl)-2-methyl-cyclopentyl]-3-methyl-penta-2,4-dienyl) triphenylphosphonium bromide. This product was used without purification in the next step of the process X+XI→XII (Example 8).

IR (paraffin oil): 3330 w, 2980 s, 2850 s, 1475 m, 1380 m, 1205 w, 1095 w, 1080 w.

MS (EI, 70 eV, 400° C.): 463 (2); 277 (12); 262 (100); 183 (63); 153 (9); 108 (22).

Starting from the 1'R,2'S,3'R,3RS-isomer mixture of the pentadienol (IX) there is obtained in the above manner the phosphonium salt (X; Ph=phenyl, $X^{1-}$=Br) as the 1'R,2'S,3'R-isomer, $[\alpha]^{20}_D$: −18.8° (c=0.085 in $CH_3OH$).

EXAMPLE 8

First Wittig Reaction X+XI→XII 200 mg (maximum 0.36 mmol) of crude (5-[2-hydroxy-5-(1-hydroxy-1-methyl-ethyl)-2-methyl-cyclopentyl]-3-methyl-penta-2,4-diphenyl)triphenylphosphonium bromide and 50 mg (0.3 mmol) of 2,7-dimethyl-2,4,6-octatriene-1,8-dial were placed in 2 ml of methylene chloride and treated with 1.5 ml of 1N sodium hydroxide solution. The reaction mixture was then stirred at room temperature for 90 minutes. For work up, the mixture was partitioned between methylene chloride and water, the aqueous phase was separated and the organic phase was dried with anhydrous magnesium sulphate and evaporated under reduced pressure. The residue was purified by column chromatography using silica gel and a 7:3 mixture of hexane and ethyl acetate.

In this manner there were obtained 33 mg (86 µmol, at least 28% of the theoretical yield) of 2,7,11-trimethyl-13-[2-hydroxy-5-(1-hydroxy-1-methylethyl)-2-methyl-cyclopentyl]-trideca-2,4,6,8,10,12-hexaenal in the form of a mixture of E/Z-isomers as an orange coloured powder. After recrystallization from hexane there were obtained 12 mg (31 µmol; at least 10% of the theoretical yield) of this product as the (all-E)-isomer.

$^1$H—NMR (400 MHz, $CDCl_3$): 9.45 [s, H—C(12')]; 7.02 [dd, J=14.4;11.9, H—C(15)]; 6.95 [d, J=11.9, H—C(14')]; 6.75 [dd, J=15.0; 11.4, H—C(11)]; 6.69 [dd; J=14.4; 11.9, H—C(15')]; 6.37 [d, J=15.0, H—C(12)]; 6.30 [d, J=11.9, H—C(14)]; 6.24 [d, J=15.7; H—C(8)]; 6.16 [d, J=11.4; H—C(10)]; 5.81 [dd, J=15.7;8.9, H—C(7)]; 2.30 [ddd, J=19.7;10.0;6.9, H—C(2)]; 2.24 [dd, J=10.0;8.9, H—C(6)]; 2.03 [s, $H_3$C(20)]; 1.99 [m, H—C(3α)]; 1.96 [s, $H_3$C(19)]; 1.88 [s, $H_3$C(20')]; 1.79 [ddd, J=12.3;8.4;3.8, H—C(4α)]; 1.68 [ddd; J=13.3;10.1;8.4, H—C(4β)]; 1.53 [dtd, J=16.1;6.9;3.8, H—C(3β), 2 OH]; 1.24 [s, $H_3$C(18)]; 1.18 (s,$H_3$C(17)]; 1.16 [s,$H_3$C(16)].

$^{13}$C—NMR (100.6 MHz, $CDCl_3$): 194.3 [C(12')];148.7 [C(14)]; 141.5 [C(13)]; 137.7 [C(8)]; 137.6 [C(15)]; 137.03 [C(13')]; 136.99 [C(12)]; 136.8 [C(9)]; 131.1 [C(14)]; 130.95 [C(10),C(7)]; 127.5 [C(15')]; 127.3 [C(11)]; 82.2 [C(5)]; 73.1 [C(1)]; 55.7 [C(6)]; 54.4 [C(2)]; 40.0 [C(4)]; 28.6 [C(17)]; 27.5 [C(16)]; 26.7 [C(18)]; 25.1 [C(3)]; 13.1 [C(19)]; 13.0 [C(20)]; 9.6 [C(20')].

IR ($CHCl_3$): 3680 w, 3620 m, 3460 w, 3015 s, 2980 s, 2415 m, 170 m, 1605 m, 1530 m, 1490 m, 1425 m, 1215 s, 1050 s, 930 m.

MS (EI, 70 eV, 270° C.): 384 (100, M$^+$); 366 (87); 326 (38); 277 (12); 222 (21); 197 (21); 183 (22); 157 (32); 145 (32); 131 (20); 119 (22); 105 (23); 95 (24); 43 (22).

UV/Vis ($CH_3COOC_2H_5$): 410 nm.

Starting from the 1'R,2'S,3'R-isomer of the phosphonium salt (X; Ph=phenyl, $X^{1-}$=Br) there is obtained in the above manner the tridecahexaenal (XII) as the 1'R,2'S,3'R-isomer.

EXAMPLE 9

Second Wittig Reaction XII+XIII→II

A solution of 59 mg (0.16 mmol) of 2,7,11-trimethyl-13-[2-hydroxy-5-(1-hydroxy-1-methylethyl)-2-methyl-cyclopentyl]-trideca-2,4,6,8,10,12-hexaenal and 94 mg (0.17 mmol) of (3,7,11-trimethyl-dodeca-2,4,6,10-tetraenyl) triphenylphosphonium bromide in 5 ml of methylene chloride was treated with 1 ml of 1N sodium hydroxide solution and the reaction mixture was heated at the reflux temperature for 90 minutes. For the working up, the solution was subsequently partitioned between ethyl acetate and water, the aqueous phase was separated and the organic phase was washed with sodium chloride solution, dried with anhydrous sodium sulphate and evaporated under reduced pressure. The residue was purified by column chromatography using silica gel and a 2:1 mixture of hexane and ethyl acetate.

In this manner there were obtained 38 mg (67 mmol; 43% of the theoretical yield) of 2,6-cyclolycopene-1,5-diol in the form of a mixture of (E/Z)-isomers as a red powder. For further purification, this can be recrystallized, for example, from hexane, which gives the (all-E)-isomer, m.p. 78° C. with decomposition.

$^1$H—NMR (300 MHz, CDCl$_3$): 6.63 [dd, J=15,0;11,1, H—C (11')]; 6.63 [dd, J=14.9;11.3, H—C(11)]; 6.63 [m, H—C (15), H—C(15')]; 6.51 [dd, J=15.1;11.0, H—C(7')]; 6.36 [d, J=14.9; H—C(12)]; 6.35 [d, J=15.0, H—C(12')]; 6.26 [d, J=15.1, H—C(18')]; 6.25 [d, J=15.7, H—C(8)]; 6.23 [m, H—C(14), H—C(14')]; 6.19 [d, J=11.1, H—C(10')]; 6.16 [d, J=11.3, H—C(10)]; 5.94 [d, J=11.0, H—C(6')]; 5.73 [dd, J=15.7;9.0, H—C(7)]; 5.16 [m, H—C(2')]; 2.30 [ddd, J=17.1;10.1;7.0, H—C(2)]; 2.23 [dd, J=10.0;9.0, H—C(6)]; 2.12 [m, H$_2$—C(3'), H$_2$—C(4')]; 1.98 [s, H$_3$C(20), H$_3$C(20')]; 1.97 [s, H$_3$C(19')]; 1.95 [m, H—C(3α)]; 1.94 [s, H$_3$C(19')]; 1.82 [s, H$_3$C(18')]; 1.79 [ddd, J=12.3;8.4;3.8, H—C(4α)]; 1.68 [s, H$_3$C(16')]; 1.67 [m, H—C(4β)]; 1.62 [s, H$_3$C(17')]; 1.53 [m, H—C(3β)]; 1.24 [s, H$_3$C(16)]; 1.19 [s, H$_3$C(18)]; 1.18 [s, H$_3$C(17)].

$^{13}$C—NMR (75,5 MHz, CDCl$_3$): 139.5 [C(5')]; 138.2 [C(8)]; 138.0 [C(12)]; 137.3 [C(12')]; 136.7 [C(13')]; 136.2 [C(13)]; 135.4 [C(8')]; 134.9 [C(9)]; 132.9 [C(14)]; 132.5 [C(14')]; 131.8 [C(1')]; 131.6 [C(10')]; 131.5 [C(10)]; 130.3 [C(15)]; 129.9 [C(15')]; 129.4 [C(7)]; 125.7 [C(6')]; 125.2 [C(11')]; 124.8 [C(7')]; 124.6 [C(11)]; 123.9 [C(2')]; 82.2 [C(5)]; 73.1 [C(1)]; 55.6 [C(6)]; 54.3 [C(2)]; 40.2 [C(4')]; 39.7 [C(4)]; 28.5 [C(16))]; 27.4 [C(17)]; 26.7 [C(3')+C(18)]; 25.7 [C(16')]; 25,1 [C(3)]; 17.7 [C17')]; 17.0 [C(18')]; 13.1 [C(19)]; 12.9 [C(19')]; 12.8 [C(20)+C(20')].

IR (CHCl$_3$): 3640 w, 3600 m, 3440 w, 3010 s, 2980 s, 2860 m, 2390 m, 1515 m, 1470 w, 1415 m, 1220 s, 1045 s.

MS (EI, 70 eV, 300° C.): 570 (52, M+); 552 (2); 478 (14); 464 (12); 223 (19); 209 (25); 159 (52); 145 (62); 133 (36); 105 (62); 91 (43); 69 (31); 55 (20); 43 (100).

UV/Vis (CH$_3$COOC$_2$H$_5$): 491, 459, 433 nm; (petroleum ether): 487, 455, 429 nm.

Starting from the 1'R,2'S,3'R-isomer of the tridecahexaenal (XII) there is obtained in the above manner 2,6-cyclolycopene-1,5-diol (II) as the all-E,2R,5R,6S-isomer having the following circular dichroism data (CD):

CD (diethyl ether:isopentane:ethanol 5:5:2, –180° C.): 216.5 (–3.8, neg. max), 228 (+1.7, pos. max), 244 (+0.2, pos. max), 283.5 (+0.6, pos. max), 297.5 (+3.0, pos. max), 443.5 (–4.9 neg. max), 455 (–3.6, pos. max), 469 (–7.2, neg. max), 498 (–3.4, pos. max), 504 (–8.5, neg. max), 515.5 (–1.4, pos max).

EXAMPLE 10

Olefination VIII→XIV 900 mg of an about 55% oily suspension sodium hydride (about 20 mmol) in petroleum were placed in 30 ml of dimethoxymethane under argon and the mixture was cooled to –30° C. Then a solution of 4.5 ml (22.5 mmol) of triethyl phosphonoacetate in 5.5 ml of dimethoxyethane was sprayed in in such a manner that the temperature always remained below –20° C. The mixture was stirred at –25° C. to –20° C. for 45 minutes and thereafter a solution of 2 g (6.67 mmol) of 4-[5-(1-hydroxy-1-methylethyl)-2-methyl-2-trimethylsilyloxy-cyclopentyl]-3-buten-2-one (prepared as described in Example in 5) in 3 ml of dimethoxyethane was sprayed in in such a manner that the temperature remained below –15° C. The solution was stirred for about 16 hours, during which it warmed to room temperature. For work up, 10 ml of saturated ammonium chloride solution were cautiously added to the solution and the separated aqueous phase was extracted three times with ethyl acetate, and the combined organic phases were washed with saturated sodium chloride solution, dried over anhydrous magnesium sulphate and evaporated under reduced pressure.

Purification of the residue was effected by flash chromatography using silica gel and a mixture of 15–40% ethyl acetate in hexane.

In this manner there were obtained 1.19 g [48% of the theoretical yield; 98% yield based on reacted cyclopentylbutanone (VIII), as 1.03 g of unreacted starting material remained] of ethyl 5-[5-(1-hydroxy-1-methylethyl)-2-methyl-2-trimethylsilyloxy-cyclopentyl]-3-methyl-penta-2,4-dienoate. The product was obtained as a colourless oil and consisted of a cis-trans isomer mixture of the pentadienoic acid ester (XIV).

$^1$H—NMR (300 MHz, CDCl$_3$): 7.55 [d,J=6.1,H—C(4)cis]; 6.16 [m,H—C(4)trans, H—C(5)]; 5.71 [s,H—C(2)trans]; 5.62 [s,H—C(2)cis]; 4.13 [m,H$_2$—C(1''')]; 2.31 [m,H—C(3')]; 2.29 [s,CH$_3$—C(3)trans]; 2.12 [m,H—C(2')]; 2.00 [s, CH$_3$—C(3)cis]; 1.96 [m,H—C(4')]; 1.80 [m,H—C(5')]; 1.55 [m,H—C(4'), H—C(5')]; 1.27 [t,J=6.2, Me(2''')]; 1.24, 1.22, 1.18, 1.16, 1.15, 1.14 [6s, CH$_3$—C(1'), CH$_3$—C(1''), CH$_3$ (2'')].

$^{13}$C—NMR (75.5 MHz, CDCl$_3$): 167.3/166.4 [C(1)]; 152.4/151,1 [C(3)]; 141.8/140.4 [C(5)]; 134.6/128.9 [C(4)]; 117.9/115.9 [C(2)]; 85.5/85.4 [C(1')]; 73.3/73.2 [C(1'')]; 59.6/59.5 [C(1''')]; 57.7/57.4 [C(2')]; 54.6/54.3 [C(3')]; 40.5 [C(5')]; 28.3/28.2 [C(2')]; 27.7/27.2 [CH$_3$—C(1')]; 26.1/25.9 [CH$_3$—C(1'')]; 25.4/25.2 [C(4')]; 21.2 [CH$_3$—C(3)]; 14,3/13,8 [C(2''')].

IR (CHCl$_3$): 3550 w, 2965 s, 2875 m, 2455 w, 1690 s, 1630 s, 1610 s, 1450 m, 1375 s, 1350 m, 1250 s, 1150 s, 1090 s, 1040 s, 1015 m, 1000 m, 975 m, 940 m. MS (EI, 70 eV, 150° C.): 368 (M+,98); 353 (12); 335 (11); 309 (98), 278 (21), 263 (21); 232 (15); 174 (20); 143 (100); 73 (34).

EXAMPLE 11

Reduction and Deprotection XIV→XV 200 mg (0.54 mmol) of ethyl 5-[5-(1-hydroxy-1-methylethyl)-2-methyl-2-trimethylsilyloxy-cyclopentyl]-3-methyl-penta-2,4-dienoate in 3 ml of hexane were cooled to –65° C. under argon and 4 ml of 1M solution of diisobutyl aluminium hydride were sprayed in such a manner that the temperature of the reaction mixture did not rise about –60° C. The solution was warmed to room temperature within an hour. Then 3 ml of saturated ammonium chloride solution were sprayed in cautiously, the separated aqueous phase was extracted three times with ethyl acetate and the combined organic phases were evaporated, dissolved in 6 ml of tetrahydrofuran and treated with 0.5 ml of 2M hydrochloric acid. The resulting solution was stirred for 30 minutes and partitioned between ethyl acetate and water, and the separated aqueous phase was extracted three times with ethyl acetate. The combined organic phases were dried over anhydrous magnesium sulphate and evaporated, and the residue was subjected to flash column chromatography using silica gel and a mixture of 30–100% ethyl acetate in hexane.

In this manner there were obtained 20 mg (14.5% of the theoretical yield) of 5-[2hydroxy-5-(1-hydroxy-1-methylethyl)-2-methyl-cyclopentyl]-3-methyl-penta-2,4-dien-1-ol as a white solid.

$^1$H—NMR (300 MHz, dimethyl sulphoxide): 6.27 [d,J= 15.8,H—C(4)]; 5.94 [d,J=15.8,H—C(4)]; 5.67 [dd,J=15.6; 8.4,H—C(5)]; 5.60 [dd,J=15.8; 8.6,H—C(5)]; 5.43 [t,J=6.6, H—C(2)]; 5.30 [t,J=6.6,H—C(2)]; 4.53 [t,J=6.6,OH]; 4.05 [m,H$_2$—C(1)]; 3.88 [t,J=6.6;OH]; 3.33 [s,OH]; 2.03 [m,H—C(2'),H—C(3')]; 1.76 [s,CH$_3$—C(3)]; 1.75 [m,H—C(5')]; 1.68 [s,CH$_3$—C(3)]; 1.56 [m,H—C(4'), H—C(5')]; 1.44 [m,H—C(4')]; 1.06/1.05/1.01/0.98/0.97 [5s,CH$_3$—C(1'), CH$_3$—C(1"),CH$_3$(2")].

$^{13}$C—NMR (75.5 MHz, dimethyl sulphoxide): 135.1/132.2 [C(5)]; 134.7/127.3 [C(4)]; 129.9/128.4 [C(2)]; 57.7/56.9 [C(1)]; 55.6/55.4 [C(2')]; 53.9/53.8 [C(3')]; 40.4/40.3 [C(5')]; 29.9/29.8/27.8/27.6/26.2 [CH$_3$—C(1'),CH$_3$—C(1"), C(2")]; 24.5 [C(4')]; 20.6/12.6 [CH$_3$—C(3)]. IR (CHCl$_3$): 3685 m, 3610 m, 3420 m, 3010 s, 2970 s, 2925 m, 1605 m, 1515 w, 1420 m, 1380 m, 1230 s, 1050 m, 1030 m, 1010 m, 975 w, 930 m. MS (EI, 70 eV, 150° C.): 236 (M$^+$-18.18); 218 (14); 203 (12); 178 (61), 160 (25), 145(25); 120 (100); 105 (39); 93 (22); 59 (18); 43 (24).

EXAMPLE 12

Phosphonium Salt Formation XV→X 20 mg (0.078 mmol) of 5-[2-hydroxy-5-(1-hydroxy-1-methylethyl)-2-methyl-cyclopentyl]-3-methyl-penta-2,4-dien-1-ol and 30 mg (0.086 mmol) of triphenylphosphonium bromide were dissolved in 2 ml of methanol and the solution was stirred at room temperature for 29 hours under nitrogen and with the exclusion of light. Thereafter, the eraction mixture was introduced into about 100 ml of ice-cold tert.butyl methyl ether and the phosphonium salt produced in this manner precipitated. After decantation of the supernatant and filtration the collected precipitate was washed with tert.butyl methyl ether and dried under reduced pressure.

In this manner there were obtained 29.3 mg (65% of the theoretical yield) of (5-[2-hydroxy-5-(1-hydroxy-1-methylethyl)-2-methyl-cyclopentyl]-3-methyl-penta-2,4-dienyl) triphenylphosphonium bromide as a white solid. This product can be converted into 2.6-cyclolycopene-1,5-diol in accordance with Examples 8 and 9.

We claim:

1. 3-(1-Acetoxy-1-methylethyl)-6-oxo-heptanal.
2. 3-(1-Acetoxy-1-methylethyl)-2-formyl-1-methyl-cyclopentanol.
3. 5-[2-Hydroxy-5-(1-hydroxy-1-methylethyl)-2-methyl-cyclopentyl]-3-methyl-penta-2,4-dien-1-ol.
4. 2,7,11-trimethyl-13-[2-hydroxy-5-(1-hydroxy-1-methylethyl)-2-methyl-cyclopentyl]-trideca-2,4,6,8,10,12-hexaenal.

* * * * *